US011678909B2

(12) United States Patent
Fayne et al.

(10) Patent No.: US 11,678,909 B2
(45) Date of Patent: Jun. 20, 2023

(54) POWERED INTRAOSSEOUS DRIVER WITH PROTECTIVE MEMBER, AND RELATED KITS, COMPONENTS, AND METHODS

(71) Applicant: TELEFLEX LIFE SCIENCES LIMITED, Valletta (MT)

(72) Inventors: Joanne Fayne, Athlone (IE); John Morgan, San Antonio, TX (US); Eugene Skelton, Dublin (IE); Anthony Wright, Dungarvan (IE)

(73) Assignee: TELEFLEX LIFE SCIENCES LIMITED, Valletta (MT)

( * ) Notice: Subject to any disclaimer, the term of this patent is extended or adjusted under 35 U.S.C. 154(b) by 394 days.

(21) Appl. No.: 16/645,988

(22) PCT Filed: Sep. 10, 2018

(86) PCT No.: PCT/IB2018/056893
§ 371 (c)(1),
(2) Date: Mar. 10, 2020

(87) PCT Pub. No.: WO2019/049098
PCT Pub. Date: Mar. 14, 2019

(65) Prior Publication Data
US 2020/0197044 A1 Jun. 25, 2020

Related U.S. Application Data
(60) Provisional application No. 62/556,953, filed on Sep. 11, 2017.

(51) Int. Cl.
A61B 17/34 (2006.01)
A61B 90/00 (2016.01)
A61B 10/02 (2006.01)

(52) U.S. Cl.
CPC ...... *A61B 17/3472* (2013.01); *A61B 17/3476* (2013.01); *A61B 17/3494* (2013.01);
(Continued)

(58) Field of Classification Search
CPC ............ A61B 17/3472; A61B 17/3494
See application file for complete search history.

(56) References Cited

U.S. PATENT DOCUMENTS 6,183,442 B1 2/2001 Athanasiou et al.
6,273,715 B1 8/2001 Meller
(Continued)

FOREIGN PATENT DOCUMENTS

CN 1520893 A 8/2004
CN 106999680 A 8/2017
(Continued)

OTHER PUBLICATIONS

International Search Report from PCT/IB2018/056893; dated Nov. 27, 2018.

*Primary Examiner* — Nicholas W Woodall
(74) *Attorney, Agent, or Firm* — BakerHostetler

(57) ABSTRACT

Powered drivers (10) for inserting an intraosseous device (160) into a bone and associated bone marrow are disclosed. Some of the powered drivers (10) may include a housing (12) having a distal end (14) and a proximal end (16); a motor (18) disposed in the housing (12); a driveshaft (34) extending outward from the distal end (14) of the housing in a direction away from the proximal end (16); a gearbox (32) coupled to the motor (18) and to the driveshaft (34) such that activation of the motor (18) causes the driveshaft (34) to rotate; and a power source (40) configured to power the motor (18). A guard member (50) may be pivotably connected to the housing (12) and movable between a protective position and a non-protective position. The guard member (Continued)

(50) may be configured to cover the intraosseous (10) needle assembly in the protective position and to expose the intraosseous (10) needle assembly in the non-protective position. A biasing member (70) may be configured to urge the guard member (50) toward the non-protective position.

20 Claims, 12 Drawing Sheets

(52) U.S. Cl.
CPC ............... *A61B 2010/0258* (2013.01); *A61B 2090/0814* (2016.02)

(56) References Cited

U.S. PATENT DOCUMENTS

| | | | |
|---|---|---|---|
| 7,699,850 B2 | 4/2010 | Miller | |
| 7,811,260 B2 | 10/2010 | Miller et al. | |
| 7,815,642 B2 | 10/2010 | Miller | |
| 8,038,654 B2 * | 10/2011 | Lim | A61M 5/3216 604/192 |
| 9,027,254 B1 | 5/2015 | Vodinh | |
| 9,433,400 B2 | 9/2016 | Miller | |
| 10,052,111 B2 | 8/2018 | Miller et al. | |
| 2014/0262880 A1 | 9/2014 | Yoon | |
| 2014/0364803 A1 * | 12/2014 | Rubinstein | A61M 5/422 604/110 |
| 2015/0190165 A1 | 7/2015 | Vodinh | |
| 2015/0230823 A1 | 8/2015 | Morgan et al. | |

FOREIGN PATENT DOCUMENTS

| | | |
|---|---|---|
| EP | 1346739 A1 | 9/2003 |
| EP | 3107692 A1 | 12/2016 |
| JP | 2003275310 A | 9/2003 |
| JP | 2008228861 A | 10/2008 |
| JP | 2016522691 A | 8/2016 |
| JP | 2017514538 A | 6/2017 |
| KR | 101064079 B1 | 9/2011 |
| WO | 2015/123660 A1 | 8/2015 |

* cited by examiner

POWERED INTRAOSSEOUS DRIVER WITH PROTECTIVE MEMBER, AND RELATED KITS, COMPONENTS, AND METHODS

CROSS-REFERENCE TO RELATED APPLICATIONS

This application is a National Stage of International Patent Application PCT/IB2018/056893, filed on Sep. 10, 2018, which claims priority to U.S. Provisional Patent Application No. 62/556,953 filed Sep. 11, 2017, the entire contents of which are incorporated herein by reference.

FIELD OF INVENTION

The present disclosure is generally related to powered drivers for inserting an intraosseous device into a patient's bone, and more particularly, but not by way of limitation, to single-use powered drivers having a protective member for the intraosseous device.

BACKGROUND

Many patients require direct vascular access for the treatment of certain medical conditions or life-threatening emergencies, such as shock, trauma, cardiac arrest, drug overdoses, diabetic ketoacidosis, arrhythmias, burns, and status epilepticus, just to name a few. An essential element for treating medical emergencies is rapid establishment of an intravenous (IV) line to administer drugs and fluids directly into the circulatory system. However, some patients may experience problems with traditional intravenous access. Obtaining satisfactory vascular access can therefore be a critical problem for some patients treated in either pre-hospital or hospital settings. For instance, doctors, nurses and paramedics may experience great difficulty establishing IV access in some patients. These patients are probed repeatedly with sharp needles in an attempt to solve this problem and may require an invasive procedure to finally establish an intravenous route. A further complicating factor in achieving IV access occurs "in the field," e.g., at the scene of an accident or during ambulance transport where it is difficult to see the target site and excessive motion can make accessing the venous system very difficult.

In the case of patients with chronic disease, or elderly patients, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. Patients with life-threatening emergencies risk death from ensuing complications when access to the vascular system with life-saving IV therapy is delayed or simply not possible. For such patients, an alternative approach utilizing intraosseous (IO) access can help. Such IO access may be achieved by using powered drivers associated with IO devices.

Conventional powered drivers typically include a housing with various types of motors and/or gear assemblies disposed therein. Many powered drivers, however, must be manually loaded prior to use, and are also intended to be reusable for many applications. Therefore, there is a need for a powered driver having a pre-loaded IO device, such as an IO needle assembly, that is releasably attached thereto for rapid insertion of the IO device into a target site of a patient. There is a further need for a protective cover for the pre-loaded IO device to prevent damage to the IO device and to prevent accidental harm to a user. There is also a need for a single-use powered driver for preventing a user from re-using the driver after insertion of the IO device into an insertion site.

SUMMARY

Embodiments of the present drivers and kits can be configured to assist a user with inserting an intraosseous (IO) device into a patient's bone.

Some embodiments of the present disclosure are directed to a driver for inserting an intraosseous needle assembly into a bone and associated bone marrow, the driver comprising a housing having a distal end and a proximal end; a motor disposed in the housing; a driveshaft extending outward from the distal end of the housing in a direction away from the proximal end; a gearbox coupled to the motor and to the driveshaft such that activation of the motor causes the driveshaft to rotate; a power source configured to power the motor; a guard member pivotably connected to the housing and movable between a protective position and a non-protective position, wherein the guard member is configured to cover the intraosseous needle assembly in the protective position and to expose the intraosseous needle assembly in the non-protective position; and a biasing member configured to urge the guard member toward the non-protective position.

In some implementations of the present disclosure, the guard member is pivotably connected to the distal end of the housing.

In some implementations of the present disclosure, the biasing member is a torsion spring.

In some implementations of the present disclosure, a proximal end of the guard member includes a first pivot part, and a distal end of the housing includes a second pivot part, wherein the first and second pivot parts are configured to engage each other to allow the guard member to pivot relative to the housing.

Some implementations of the present disclosure further comprise a generally cylindrical retention collar provided within the distal end of the housing and surrounding the driveshaft to define an annular gap therebetween, and wherein an axis of the retention collar is substantially aligned with an axis of the driveshaft when the guard member is oriented in the protective position.

Some implementations of the present disclosure further comprise a pair of locking notches extending from the first pivot part of the guard member, and a pair of corresponding retention tabs extending upwardly from the collar, wherein the pair of locking notches are configured to engage the pair of retention tabs when the guard member is oriented in the protective position.

Some implementations of the present disclosure further comprise a pair of oppositely spaced apart release buttons extending from opposed ends of the retention collar, wherein activating the pair of release buttons moves the retention collar laterally relative to the driveshaft to disengage the pair of retention tabs from contacting the corresponding pair of locking notches, thereby allowing the biasing member to pivot the guard member from the protective position to the non-protective position.

In some implementations of the present disclosure, the guard member comprises a needle groove configured to receive an intraosseous needle.

In some implementations of the present disclosure, the guard member comprises a distal tip having a smooth bulbous shape.

Some implementations of the present disclosure further comprise a sharps receptor defining an opening provided in the proximal end of the housing and configured to receive an intraosseous needle.

Some implementations of the present disclosure further comprise a flexible sharps guide and an interior support shelf, the sharps guide being located within the proximal end of the housing and configured to guide the intraosseous needle as it is received into the housing, and the interior support shelf being located within the proximal end of the housing and configured to support the intraosseous needle as it is received into the housing.

In some implementations of the present disclosure, the sharps guide comprises a guide slot for receiving and guiding the intraosseous needle as it is inserted into the housing, and wherein the interior support shelf and the sharps guide are both configured to securely retain the intraosseous needle within the housing such that the sharps guide is biased toward the interior support shelf.

In some implementations of the present disclosure, the sharps guide is a leaf spring.

Some implementations of the present disclosure further comprise a trigger configured to close an electrical circuit between the power source and the motor upon activation of the trigger in order to rotate the driveshaft.

In some implementations of the present disclosure, the housing defines a primary portion extending between the distal end and the proximal end, and a handle extending laterally from the primary portion at a non-parallel angle relative to a longitudinal axis of the primary portion.

In some implementations of the present disclosure, the handle defines a hollow compartment for storing the power source.

Some implementations of the present disclosure further comprise an end cap connected to the handle by at least one frangible member configured to break or snap upon application of a threshold force to cause the end cap to detach from the handle, and thereby cause the power source to fall out from the compartment of the handle.

In some implementations, the end cap further includes a grip portion defining a recess sized and shaped for receiving a user's thumb or other finger so that the user can laterally grip the end cap in order to facilitate pulling or rotating the end cap relative to the handle to break the at least one frangible member.

In some implementations of the present disclosure, the power source comprises at least one battery.

In some implementations of the present disclosure, at least a portion of the driveshaft has an equilateral polygonal cross-sectional shape.

In some implementations of the present disclosure, the at least a portion of the driveshaft has a pentagonal cross-sectional shape.

In some implementations of the present disclosure, a top surface of the handle comprises a guard recess having a shape corresponding to the shape of the guard member for receiving the guard member when in the non-protective position.

Some implementations of the present disclosure further comprise an electrical lockout comprising a strip configured to be removably inserted into the housing between two electrically conductive portions of the electrical circuit to prevent the apparatus from energizing during sterilizing or transporting.

In some implementations of the present disclosure, the strip comprises a polymer. In some implementations of the present disclosure, the polymer comprises Mylar.

Some embodiments of the present disclosure are directed toward a kit comprising the driver discussed above and an intraosseous device comprising a connector be coupled to the driveshaft of the driver; and wherein the guard member of the driver is oriented in a protective position.

In some implementations of the present disclosure, the connector comprises a recess configured to receive a distal end of the driveshaft.

In some implementations of the present disclosure, the intraosseous device comprises: a hub; a cannula extending from the hub to a distal end spaced from the hub; a trocar extending from the connector to a distal end spaced from the connector; and wherein the cannula is configured to be inserted into the cannula and the connector coupled to the hub to hold the trocar in fixed relation to the cannula.

In some implementations of the present disclosure, the connector is configured to be coupled to the hub by a Luer lock connector.

In some implementations of the present disclosure, the connector comprises a female threaded portion surrounding a portion of the trocar, the hub comprises a male threaded portion extending away from the distal end of the cannula, and the male threaded portion is configured to be coupled to the female threaded portion to couple the connector to the hub.

Some embodiments of the present disclosure are directed toward a method for inserting an intraosseous needle assembly into a bone and associated bone marrow, the method comprising: providing a driver according to any one of claims 1-25, the intraosseous needle assembly being coupled to a driveshaft of the driver, and the driver having a guard member oriented in a protective position; manipulating a retention collar to pivot the guard member from the protective position to a non-protective position; disposing a distal end of the intraosseous needle assembly at a desired insertion site on a patient; actuating a trigger of the driver to activate the motor to rotate the driveshaft and the intraosseous needle assembly; inserting a portion of the intraosseous needle assembly into the insertion site; applying an amount of force to an end cap of a handle of the driver to detach the end cap and remove the power source; and removing a component of the needle assembly from the insertion site and inserting the component into a sharps receptor provided in the housing of the driver.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent. Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments. Some details associated with the embodiments described above and others are described below.

BRIEF DESCRIPTION OF THE DRAWINGS

The following drawings illustrate embodiments of the disclosure by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present drivers and intraosseous (IO) devices, and their components shown in the figures, are not necessarily drawn to scale.

DETAILED DESCRIPTION

Figure 1A:
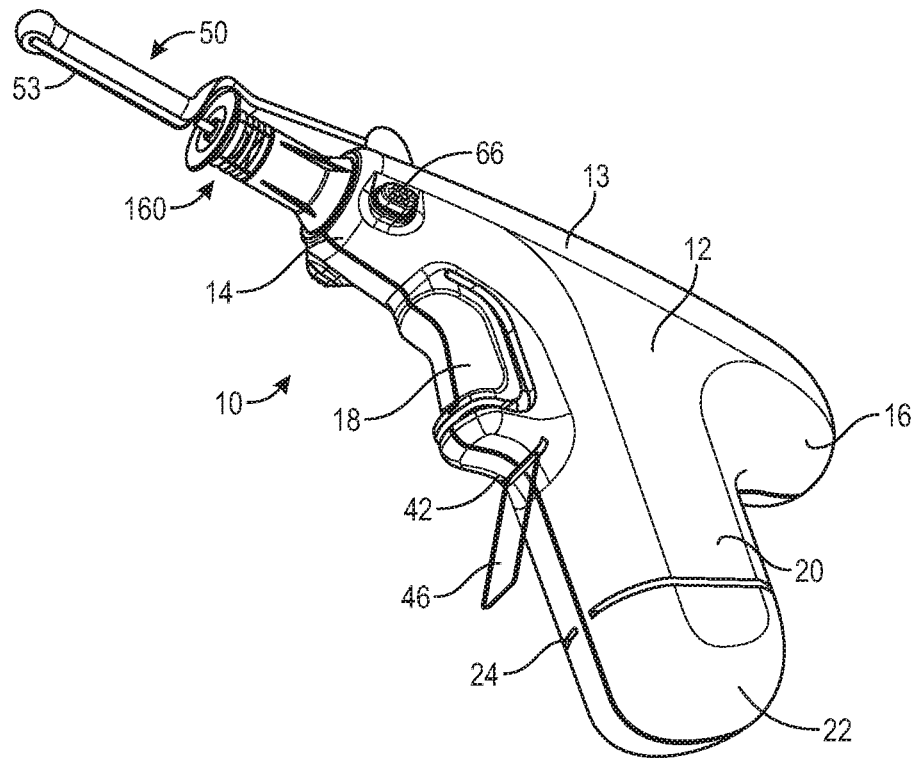
FIGS. 1A and 1B depict respective bottom and top isometric views of an embodiment of the driver assembly and the intraosseous device of the present disclosure.

Vascular system access may be essential for treatment of many serious diseases, chronic conditions, and acute emergency situations. Yet, many patients experience extreme difficulty obtaining effective treatment because of an inability to obtain or maintain intravenous (IV) access. An intraosseous (IO) space provides a direct conduit to a patent's vascular system and systemic circulation. Therefore, IO access is generally an effective route to administer a wide variety of drugs, other medications, and/or IV fluids. Moreover, rapid IO access or emergency vascular access (EVA) offers great promise for a wide range of serious emergencies that require vascular access to administer life-saving drugs, other medications, and/or fluids when traditional IV access is difficult or impossible.

Bone marrow typically includes blood, blood forming cells, and connective tissue disposed in an intraosseous space or cavity surrounded by compact bone. Long bones such as the tibia typically have an elongated central cavity filled with yellow bone marrow and adipose or connective tissue. Such cavities may also be referred to as a "medullary cavity," "bone marrow cavity," and/or "intraosseous space." Compact bone disposed near an anterior or dorsal surface may be referred to as "anterior compact bone" or "anterior bone cortex." Compact bone disposed farther from the dorsal or anterior surface may be referred to as "posterior compact bone" or "posterior bone cortex." Embodiments of the present powered drivers may be used to insert an IO device incorporating teachings of the present disclosure into a selected target area or target site (e.g., in ten seconds or less).

Examples of insertion sites for an IO device to establish access with a patient's vascular system include the upper tibia proximate a patient's knee, the lower tibia, the humeral head proximate a patient's shoulder, and the patient's sternum. Other desired insertion sites may be disposed over a distal portion of the patient's femur, a patient's clavicle, a patient's iliac crest, or a patient's calcaneous. Availability of multiple intraosseous insertion sites and associated target areas in adjacent bone marrow have proven to be particularly important in applications such as emergency treatment of battlefield casualties or other mass casualty situations. Teachings of the present disclosure may be used to obtain intraosseous access at a wide variety of insertion sites and target areas.

IO access may be used as a "bridge" for temporary fluid and/or drug therapy during emergency conditions until conventional IV sites can be found and used. Conventional IV sites often become available because fluids and/or medication provided via IO access may stabilize a patient and expand veins and other portions of a patient's vascular system. IO devices and associated procedures incorporating teachings of the present disclosure may become standard care for administering medications and fluids in situations when IV access is difficult or otherwise impossible.

Intraosseous access may be used as a "routine" procedure with chronic conditions which substantially reduce or eliminate availability of conventional IV sites. Examples of such chronic conditions may include, but are not limited to, dialysis patients, patients in intensive care units, and/or epilepsy patients. Intraosseous devices and associated apparatuses incorporating teachings of the present disclosure may be quickly and safely used to provide IO access to a patient's vascular system in difficult cases, such as status epilepticus, to give medical personnel an opportunity to administer crucial medications and/or fluids. Further examples of such acute and chronic conditions are listed near the end of this written description.

Apparatuses and methods incorporating teachings of the present disclosure may include using a first IO needle set having a (e.g., a fifteen (15) gauge) cannula with a length of approximately fifteen (15) millimeters to establish vascular access for patients weighing between approximately three (3) kilograms and thirty nine (39) kilograms. A second IO needle set having a (e.g., a fifteen (15) gauge) cannula with an approximate length of twenty-five (25) millimeters may be used to establish vascular access for patients weighing forty (40) kilograms and greater. In other embodiments, a single size of IO needle set having a (e.g., a fifteen (15) gauge) cannula with an approximate length of twenty-five (25) millimeters may be used to establish vascular access for patients weighing three (3) kilograms and greater.

The term "driver" may be used in this application to include any type of powered driver satisfactory for inserting an intraosseous (IO) device such as a penetrator assembly, a catheter, an IO needle, and/or an IO needle set into a selected portion of a patient's vascular system. Various techniques may be satisfactorily used to releasably engage or attach an IO device with a driver incorporating teachings of the present disclosure. A wide variety of connectors and associated connector receptacles, fittings, and/or other types of connections with various dimensions and configurations may be satisfactorily used to releasably engage an IO device with a driver. A battery powered driver incorporating teachings of the present disclosure may be used to insert an intraosseous device into a selected target area in ten (10) seconds or less. The reduced size and weight of drivers incorporating teachings of the present disclosure may accommodate use in emergency medical vehicles, in emergency crash carts at medical facilities, and/or in carrying inside backpacks of military personnel deployed for extended periods of time in remote locations.

The term "fluid" may be used in this application to include liquids such as, but not limited to, blood, water, saline solutions, IV solutions, plasma, any mixture of liquids, particulate matter, dissolved medication, and/or drugs associated with biopsy and/or aspiration of bone marrow, and/or communication of fluids with bone marrow or other target sites. The term "fluid" may also be used in this patent application to include any body fluids and/or liquids containing particulate matter such as bone marrow and/or cells which may be withdrawn from a target area.

The term "insertion site" may be used in this application to describe a location on a bone at which an intraosseous device may be inserted or drilled into the bone and associated bone marrow. Insertion sites are generally covered by skin and soft tissue. The term "target area" refers to any location on or within biological material, such as the biological material of a human being.

The term "intraosseous (IO) device" may be used in this application to include, but is not limited to, any hollow needle, hollow drill bit, penetrator assembly, bone penetrator, catheter, cannula, trocar, stylet, inner penetrator, outer penetrator, IO needle, biopsy needle, aspiration needle, IO needle set, biopsy needle set, and/or aspiration needle set operable to access or provide access to an intraosseous space or interior portions of a bone. Such IO devices may be formed, at least in part, from metal alloys such as 304 stainless steel and/or other biocompatible materials associated with needles and similar medical devices.

For some applications an IO needle or IO needle set may include a connector with a trocar or stylet extending from a first end of the connector. A second end of the connector may be operable to be releasably engaged with a powered driver incorporating teachings of the present disclosure. An IO needle or IO needle set may also include a hub with a hollow cannula or catheter extending from a first end of the hub. A second end of the hub may include an opening sized to allow inserting the trocar through the opening and the attached hollow cannula. The second end of the hub may be operable to be releasably engaged with the first end of the connector. As previously noted, the second end of the connector may be releasably engaged with a powered driver. A wide variety of connectors and hubs may be used with an IO device incorporating teachings of the present disclosure.

Figure 1B:
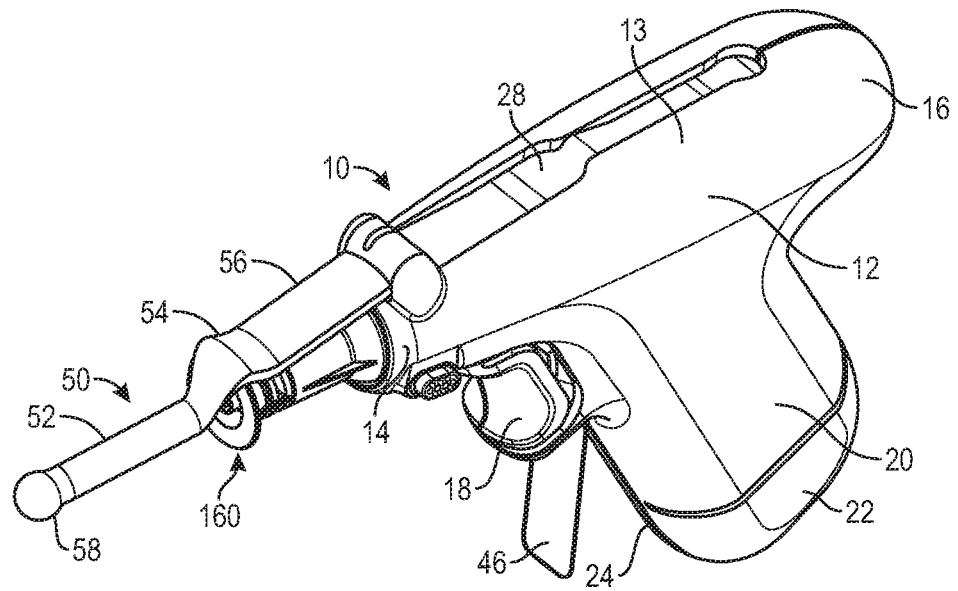
Figure 2A:
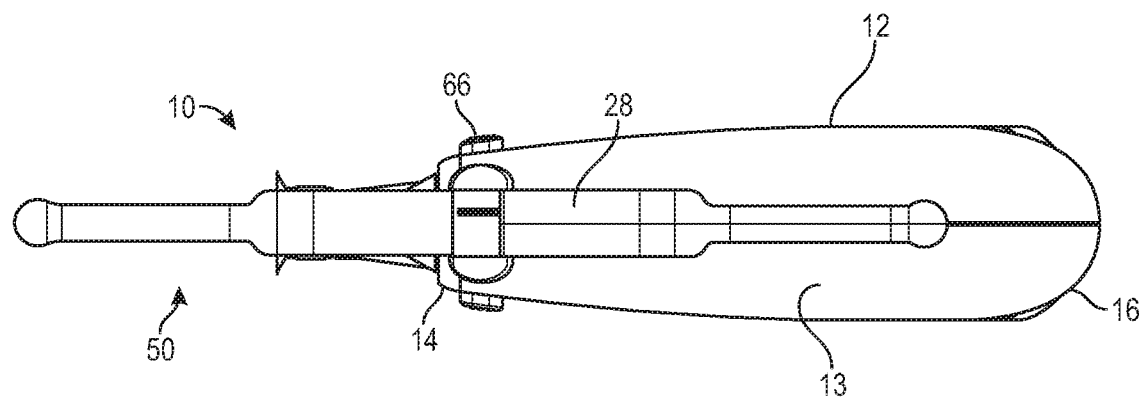
FIG. 2A depicts a top plan view of the driver assembly and the intraosseous device of the present disclosure.
Figure 2B:
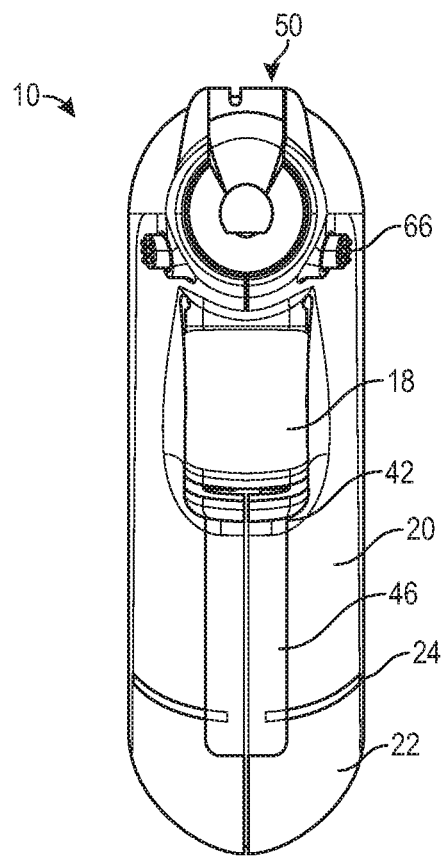
FIGS. 2B and 2C depict a front elevation view and a rear elevation view, respectively, of the driver assembly and the intraosseous device of the present disclosure.
Figure 2C:
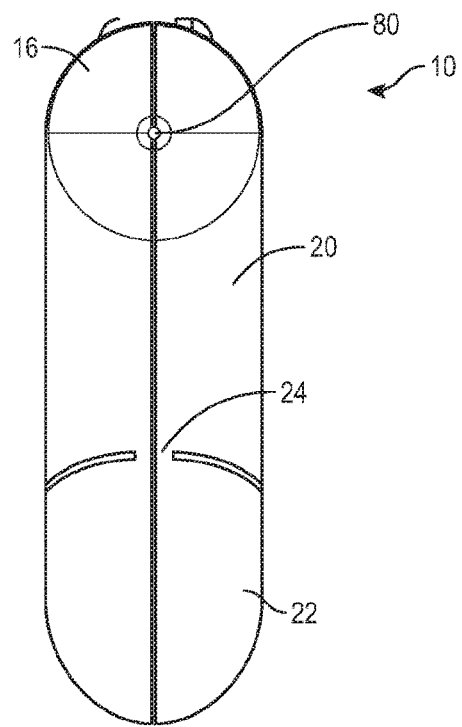
Figure 3:
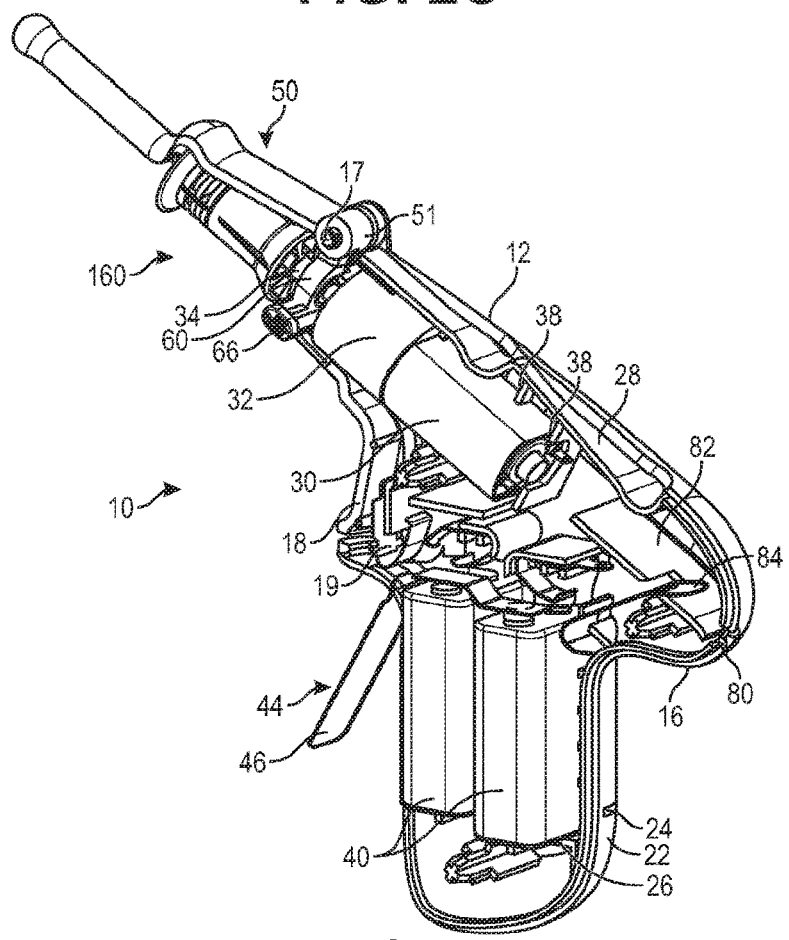
FIG. 3 depicts a partial cross-sectional perspective view of the driver assembly and the intraosseous device of the present disclosure.

FIGS. 1-3 illustrate a powered driver 10 configured to insert an IO device, such as an IO needle set 160, at a desired insertion site adjacent to a bone and associated bone marrow. The driver 10 may include one or more of the present features. The driver 10 comprises a housing 12 having a distal end 14 and a proximal end 16. The proximal end 16 of the housing may include a sharps receptor 80 configured to receive a portion of the IO device, as will be discussed in greater detail below. The housing 12 defines a primary portion or barrel portion 13 extending between the distal end 14 and the proximal end 16, and a handle 20 extending laterally from the primary portion 13. The handle 20 may extend from the primary portion 13 at a non-parallel angle (e.g., between thirty degrees (30°) and sixty degrees (60°), and in some embodiments, up to, including, or greater than ninety degrees (90°) relative to the longitudinal axis of the primary portion 13. In some implementations, the housing 12 and the handle 20 may have an optimal ergonomic form factor (i.e., resembling a pistol-grip in the illustrated embodiments). The handle 20 defines an elongated, hollow compartment sized to receive a removable power source 40, such as batteries as shown in FIG. 3. The housing 12 may be formed from heavy-duty polymeric material, or other strong material. For some applications, the housing 12 may be formed in two halves which are joined together to form a fluid tight seal with certain components of driver 10 disposed in the housing, as shown. For example, two halves of the housing 12 may be glued, welded, snapped, secured with screw fasteners, or otherwise coupled together such that the housing generally cannot be reopened (e.g., to replace batteries) without damaging the housing.

The driver 10 may be configured as a single-use driver to prevent a second activation for inserting a second IO device into a patient. Preventing re-use of the driver maintains efficacy and promotes patient safety. In the embodiment shown, an end cap 22 is coupled to the handle 20 by a pair of frangible members 24, such as tabs. The frangible members 24 are configured to break or snap in response to a user twisting, rocking, or pulling the end cap 22 relative to the handle 20 with a sufficient amount of force. Thus, after a user completes successful insertion of an IO device into a target area of a patient, the user can manually break or snap the frangible members 24 by applying a sufficient amount of force to the end cap 22 via twisting, rocking, or pulling in order to breakaway the end cap 22 from the handle 20. The end cap 22 is not removable from the handle 20 without breaking the frangible members 24, and thus also damaging the end cap and/or the handle. The end cap 22 includes at least one internal protrusion or shelf 26 configured to support the batteries 40 within the hollow compartment of the handle 20.

Once the frangible members 24 are broken and the end cap 22 is decoupled from the handle 20, the batteries 40 are no longer supported by the internal protrusion 26 of the end cap 22, thus causing the batteries to fall out from the hollow compartment of the handle. Moreover, once the frangible members 24 are snapped or broken, the end cap 22 can no longer be reconnected to the handle 20 without the use of some supplemental bonding or fixing element, such as adhesive. Accordingly, the driver 10 may be used as a single-use device, whereby after insertion of the IO device in a target site of a patient is completed, the user can manually break off the end cap 22 from the handle 20 to allow easy removal and safe disposal of the batteries 40.

According to other aspects of the disclosure, the driver 10 may be configured to allow removal of the batteries 40 by pressing the frangible tabs located on each side of the handle 20 until the tabs break, thus causing the end cap 22 to disconnect from the handle. As previously explained, removing the end cap from the handle causes the batteries to be released from driver, such as from the bottom of the handle, and can therefore render the driver inoperable for future use.

As shown in FIG. 3, the powered driver 10 further comprises a motor 30, a gearbox 32, and a driveshaft 34. The motor 30 is disposed within the housing 12, with the driveshaft 34 extending outwardly from the distal end 14 of the housing in a direction away from proximal end 16 of the housing, such that a distal end 36 of the driveshaft 34 is spaced apart from the distal end 14 of the housing. In the embodiment shown, gearbox 32 is coupled to the motor 30 and to the driveshaft 34 such that activation of the motor will cause rotation of the driveshaft. In this embodiment, the driver 10 also comprises a power source including at least one battery (e.g., two batteries 40, as shown) configured to power the motor 18 (e.g., through an electrical communication between the batteries 40 and the motor 18, for example, through electrical wiring, circuitry, and/or the like). In some implementations of the driver 10, the power source may be two 9-volt batteries which may be commercially available from a variety of suppliers and retail outlets. Other embodiments can include any suitable battery and/or combination of batteries that permit the function(s) described in this disclosure.

In the depicted embodiment, the driver 10 further includes a trigger 18 configured to be squeezed or otherwise depressed with a user's finger during use to activate the motor 30. The trigger 18 may be integrally formed with the housing 12. In this embodiment, the trigger 18 is configured to close the electrical circuit between the power source 40 and the motor 30 upon application of a threshold force on the trigger to move the trigger to an "on" or activated position. The trigger 18 is normally biased to an "off" or non-activated position in which the electrical circuit between the power source 40 and the motor 30 is open. A conductive biasing member 19, such as a leaf spring, may bias the trigger 18 to the off position, such that in the absence of the threshold force on the trigger, the electrical circuit between the power source 40 and the motor 30 remains open and the motor is therefore not activated.

In this embodiment, the motor 30, the gearbox 32, and the driveshaft 34 are coupled in fixed axial relation to each other within the housing 12 (e.g., along the longitudinal axis of the primary portion 13 of the housing). Additionally, the housing 12 may include one or more internal tabs or portions 38 on which the motor 30 and the gearbox 32 are mounted or otherwise supported (e.g., the internal tabs or portions are configured to support the motor 30 and the gearbox 32 in coaxial alignment with each other and physically prevent axial or lateral movement thereof). Motors and gear assemblies satisfactory for use with a powered driver incorporating features of the present disclosure may be obtained from various vendors. Such motor and gear assemblies may be ordered as "sets" with one end of each motor securely attached to an adjacent end of an associated gear assembly. A driveshaft having various dimensions and/or configurations may extend from the gear assembly opposite from the motor. The gear assemblies may further be referred to as "reduction gears" or "planetary gears." The dimensions and/or configurations of an associated housing may be modified to accommodate an associated motor and gear assembly. In some embodiments, the motor may be configured to rotate at a satisfactory speed and a satisfactory torque such that the gearbox is omitted and the motor directly drives the driveshaft.

The driver 10 may further comprise a slot 42 formed in the handle 20 of the housing 12. The slot 42 is configured to receive a portion of an electrical lockout or electrical interrupt 44 to prevent accidental activation of the driver 10 for increased safety when handling the driver 10, and also to permit ethylene oxide (EtO) sterilization. The slot 42 is sized and positioned to allow a portion of the electrical lockout 44 to be inserted into the housing 12 to prevent the electrical circuit from being closed, thereby preventing energizing the driver 10 when the trigger 18 is pressed (e.g., to prevent activation of the driver during sterilization, packaging, transportation, or the like). In other embodiments, the slot 42 may be located in the housing 12 closer to the primary portion 13 of the housing and still physically prevent the electrical circuit from being closed when the trigger 18 is pressed to avoid accidental activation of the motor.

The electrical lockout 44 is configured to increase safety when handling the driver 10, such as during transportation or sterilization. The electrical lockout 44 comprises a flexible strip 46 that is removably inserted into the slot 42 in the handle 20 of the housing 12 between two electrically conductive portions of the electrical circuit to prevent the driver 10 from energizing during sterilization. The flexible strip 46 may comprise a polymer, such as Mylar, and/or other non-conductive material. The strip 46 of the electrical lockout 44 can be removed from the handle in a single pull in order to allow an electrical connection between the motor 30 and the power source 40 when the trigger 18 is pressed.

In the embodiments shown, distal end 14 of the housing 12 includes an opening 15 with a portion of the driveshaft 34 extending therethrough. Further, the driveshaft 34 may include an annular groove 35 configured to receive an O-ring (e.g., a resilient polymeric or rubber O-ring) disposed around the driveshaft 34 and between the gearbox 32 and the distal end 14 of the housing 12 to seal the opening 15. In some embodiments, at least a portion (e.g., distal end 36) of the driveshaft 34 has an equilateral polygonal cross-sectional shape. For example, in the embodiment shown, a portion of the driveshaft terminating in the distal end 36 has a pentagonal cross-sectional shape defined by five surfaces 37. In some embodiments, such as the one shown, the surfaces 37 may be tapered and/or disposed at an angle relative to the longitudinal axis of the driveshaft 34 (e.g., an angle of three degrees (3°)±two degrees (2°) relative to the longitudinal axis). In some embodiments, a magnet can be disposed on and/or in the distal end 36 of the driveshaft 34 (e.g., or the distal end of the driveshaft may otherwise be magnetic). Fittings and/or connectors with various dimensions and/or configurations other than the depicted configuration of distal end 36 of the driveshaft may also be used with the powered driver 10 of the present disclosure. For example, in the implementation shown, the distal end 36 of the driveshaft 34 may be configured to releasably secure an IO needle set 160. In other implementations, driveshaft 34 may be configured to releasably secure other IO needle sets and may comprise additional associated structure.

Figure 4A:
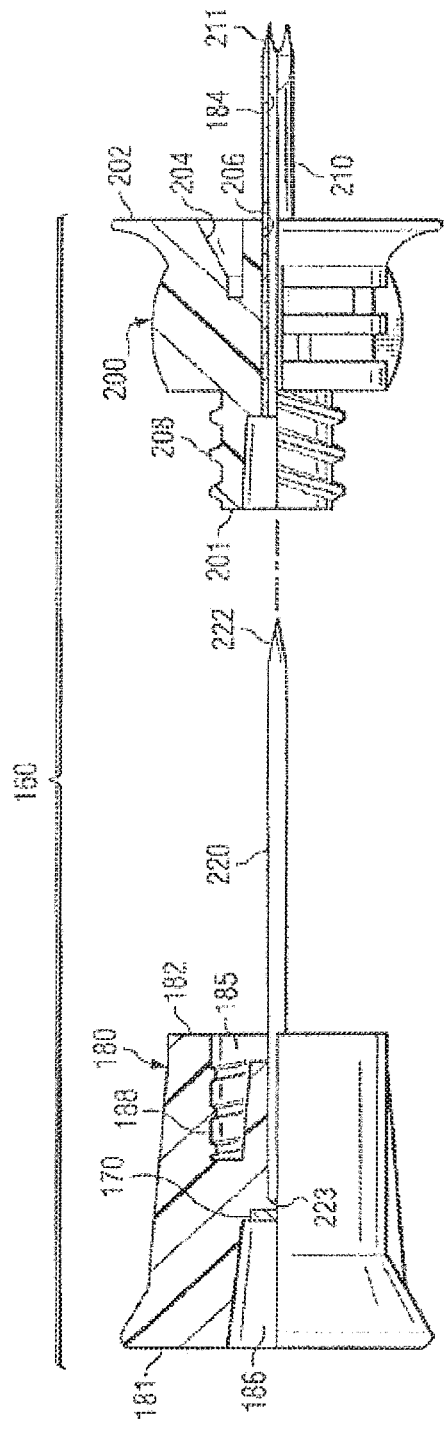
FIG. 4A depicts an exploded and partially cutaway side view of one example of an intraosseous device, such as an intraosseous needle set or penetrator assembly which may be inserted into a patient's bone and, thus, into a patient's vascular system using one of the present drivers and may be included in certain ones of the present kits.
Figure 4B:
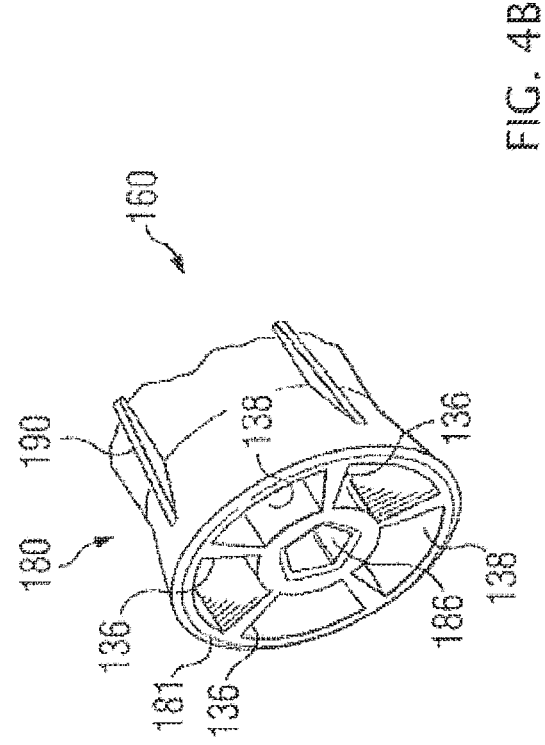
FIG. 4B depicts a partial perspective view of a connector receptacle of the IO needle set of FIG. 4A that may be releasably engaged with embodiments of the present powered drivers.

Intraosseous (IO) devices having corresponding tapered openings or connector receptacles may be releasably engaged with the distal end 36 of the driveshaft 34. For example, the distal end 36 may be releasably engaged with a tapered opening (e.g., 186) in a connector (e.g., 180) as illustrated in FIGS. 4A and 4B, which depict an example of an IO device or penetrator assembly 160 that is usable with the driver 10 of the present disclosure. The penetrator assembly 160 may include a connector 180, an associated hub 200, an outer penetrator 210, and an inner penetrator 220. The penetrator assembly 160 may include an outer penetrator such as a cannula, a hollow tube or hollow drill bit, and an inner penetrator such as a stylet or trocar. Various types of stylets and/or trocars may be disposed within an outer penetrator. For some applications, an outer penetrator or cannula 210 may be described as a generally elongated tube sized to receive an inner penetrator or stylet 220 therein. Portions of inner penetrator 220 may be disposed within a longitudinal passageway 184 extending through outer penetrator 210. The outside diameter of the inner penetrator 220 and the inside diameter of the longitudinal passageway 184 may be selected such that the inner penetrator 220 may be slidably disposed within the outer penetrator 210. It should be appreciated that the present disclosure is not limited to the connector 180 or the hub 200 shown in FIGS. 4A and 4B, which are representative of a variety of devices and components that can be used with embodiments of the present drivers and kits.

A metallic disc 170 may be disposed within the opening 186 for use in releasably attaching the connector 180 with a magnet disposed on the distal end 36 of driveshaft 34 (e.g., or an otherwise magnetic driveshaft 34). An end 223 of the inner penetrator 220 may be spaced from the metallic disc 170 with insulating or electrically nonconductive material disposed therebetween. In some embodiments, the metallic disc 170 may be magnetic and the drive shaft 34 and/or its distal end 36 may comprise metallic materials configured to releasably attach to the magnetic metallic disc of the connector 180.

A tip 211 of the outer penetrator 210 and/or a tip 222 of the inner penetrator 220 may be operable to penetrate bone and associated bone marrow. The configuration of the tips 211 and/or 222 may be selected to penetrate a bone or other body cavities with minimal trauma. A first end or tip 222 of the inner penetrator 220 may be trapezoid-shaped and may include one or more cutting surfaces. In one embodiment, outer penetrator 210 and inner penetrator 220 may be ground together as one unit during an associated manufacturing process. Providing a matching fit allows respective tips 211 and 222 to act as a single drilling unit, which facilitates insertion and minimizes damage as portions of the penetrator assembly 160 are inserted into a bone and associated bone marrow. The outer penetrator 210 and/or the inner penetrator 220 may be formed from stainless steel, titanium, and/or other materials of suitable strength and durability to penetrate bone.

The hub 200 may be used to stabilize penetrator assembly 160 during insertion of an associated penetrator into a patient's skin, soft tissue, and adjacent bone at a selected insertion site. A first end 201 of the hub 200 may be operable for releasable engagement or attachment with the associated connector 180. A second end 202 of the hub 200 may have a size and configuration compatible with an associated insertion site for outer penetrator 210. The combination of the hub 200 with the outer penetrator 210 may sometimes be referred to as a "penetrator set" or "intraosseous needle." The connector 180 and the attached inner penetrator 220 may be releasably engaged with each other by Luer type fittings, threaded connections, and/or other suitable fittings formed on the first end 201 of the hub 200. The outer penetrator 210 extends from the second end 202 of the hub 200.

In some implementations, the connector 180 may include a generally cylindrical tube defined in part by a first end 181 and a second end 182. The exterior of the connector 180 may include an enlarged tapered portion adjacent to the first end 181. A plurality of longitudinal ridges 190 may be formed on the exterior of the connector 180 in order to allow an operator to grasp the associated penetrator assembly 160 during attachment with the driveshaft 34. Longitudinal ridges 190 also allow the connector 180 to be grasped for disengagement from the hub 200 when the outer penetrator 210 has been inserted into a bone and associated bone marrow. The second end 182 of the connector 180 may include an opening 185 sized to receive the first end 201 of the hub 200 therein. Threads 188 may be formed in the opening 185 adjacent to the second end 182 of the connector 180. The threads 188 may be used to releasably attach the connector 180 with a threaded fitting 208 adjacent to the first end 201 of the hub 200. The first end 201 of the hub 200 may include a threaded connector 208 and/or other suitable fittings formed on the exterior thereof. The first end 201 may have a generally cylindrical pin-type configuration compatible to releasably engage the second end or box end 182 of the connector 180. Further, the end 202 of the hub 200 may include a flange and an angular slot or groove 204 sized to receive one end of a protective cover or needle cap.

In some implementations, the penetrator assembly may include only a single, hollow penetrator. In other implementations, the penetrator assembly may include an outer penetrator such as a cannula, a hollow needle or hollow drill bit, and an inner penetrator such as a stylet, trocar or other removable device disposed within the outer penetrator. Penetrator 210 is one example of a single, hollow penetrator or cannula. The size of the penetrator may vary depending on the intended application for the associated penetrator assembly. Penetrators may be relatively small for pediatric patients, medium size for adults, and large for oversize adults. By way of example, a penetrator may range in length from five (5) mm to thirty (30) mm. The diameter of a penetrator may range from eighteen (18) gauge to ten (10) gauge. The length and diameter of the penetrator used in a particular application may depend on the size of a bone to which the apparatus may be applied. Penetrators may be provided in a wide variety of configurations depending upon intended clinical purposes for insertion of the associated penetrator. For example, there may be one configuration for administering drugs and/or fluids to a patient's bone marrow and an alternative configuration for sampling bone marrow and/or blood from a patient. Other configurations may be appropriate for bone and/or tissue biopsy.

In some implementations, the connector 180 may have a generally cylindrical configuration defined in part by the first end 181 and the second end 182. Exterior portions of the connector 180 may include an enlarged tapered portion adjacent to the first end 181. A plurality of longitudinal ridges 190 may be formed on the exterior of the connector 180 to allow an operator to grasp the associated penetrator assembly 160 during attachment with a driveshaft 34. Longitudinal ridges 190 also allow the connector 180 to be grasped for disengagement from the hub 200 when the outer penetrator 210 has been inserted into a bone and associated bone marrow. A first end 181 of the connector 180 may include an opening 186 sized to receive portions the driveshaft 32 therein. A plurality of webs 136 may extend radially outward from the connector receptacle 186. The webs 136 may cooperate with each other to form a plurality of openings 138 adjacent to the first end 181. Opening 186 and the plurality of openings 138 may cooperate with each other to form portions of a connector receptacle operable to receive respective portions of a connector therein.

Embodiments of an intraosseous kit may include the powered driver 10 and the IO device (e.g., needle set 160) of the present disclosure. In some implementations, the components of the kit may be sterile and come ready to use with the IO needle set 160 already coupled to the driveshaft 32 of the driver 10 so that a user can quickly use the driver to insert the IO device into a target site of a patient shortly after opening the kit. Providing the driver 10 pre-loaded with the IO needle set 160 minimizes the IO procedure steps. An elongated guard member 50 may be connected to the distal end 14 of the housing 12. The guard member 50 is configured to cover the IO needle set 160 when the driver 10 is not in use in order to prevent accidental injury to a user, as well as to protect the components of the IO device from being damaged when not in use. The guard member 50 may include a needle section 52, a hub section 54, and a connector section 56, each of which are configured to correspondingly cover the respective needle 210/220, the hub 200, and the connector 180 of the IO needle set 160. In some implementations, a bottom surface of the guard member 50 may be concave in order to closely conform to the contours of the IO device.

Figure 5A:
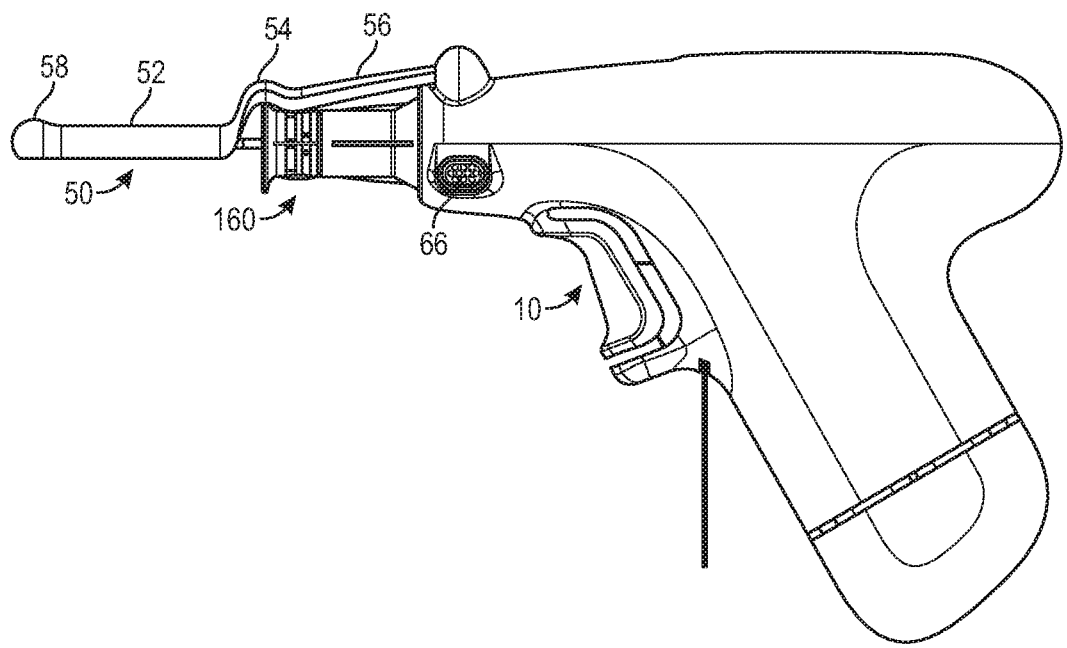
FIG. 5A illustrates a side elevation view of the driver assembly and the intraosseous device of the present disclosure with a needle guard in a protective position over the IO needle set of FIGS. 4A-4B coupled to a driveshaft of the driver.
Figure 5B:
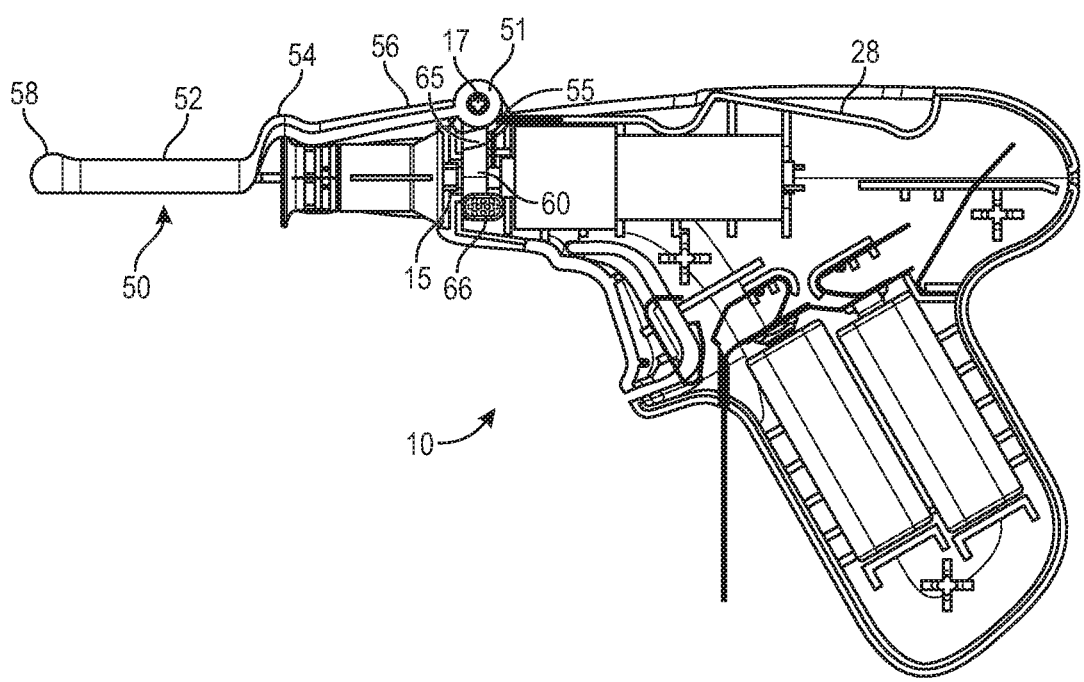
FIG. 5B illustrates a partial cross-sectional side view of the driver assembly of the present disclosure with a needle guard in a protective position over the IO needle set of FIGS. 4A-4B coupled to a driveshaft of the driver.
Figure 7A:
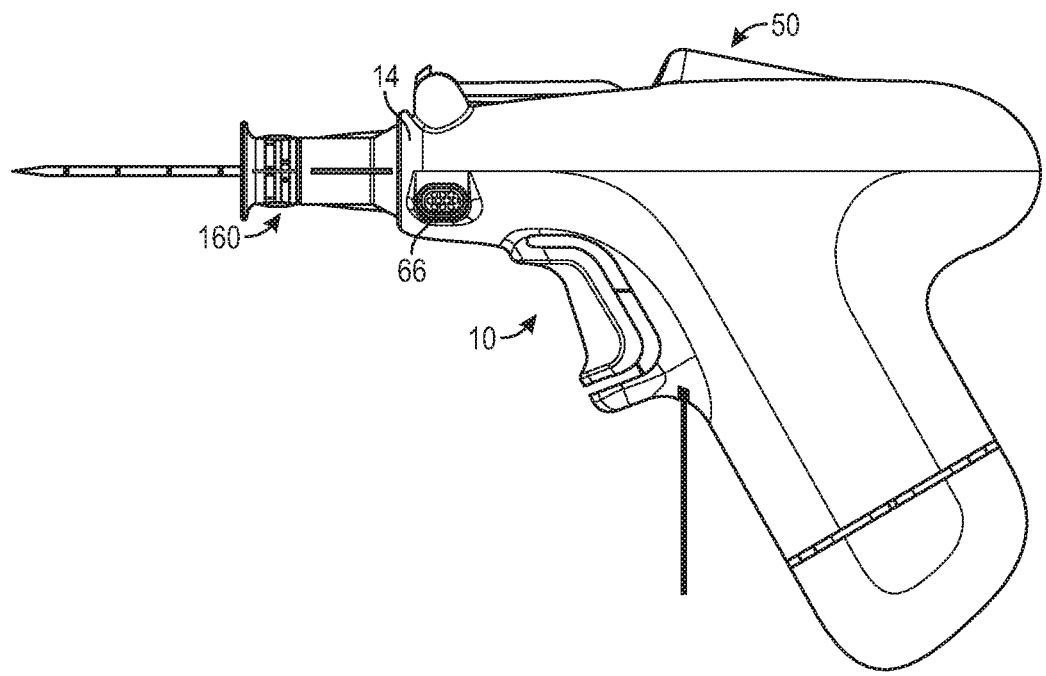
FIG. 7A illustrates a side elevation view of the driver assembly of the present disclosure with a needle guard in a non-protective position with respect to the IO needle set of FIGS. 4A-4B coupled to a driveshaft of the driver.
Figure 7B:
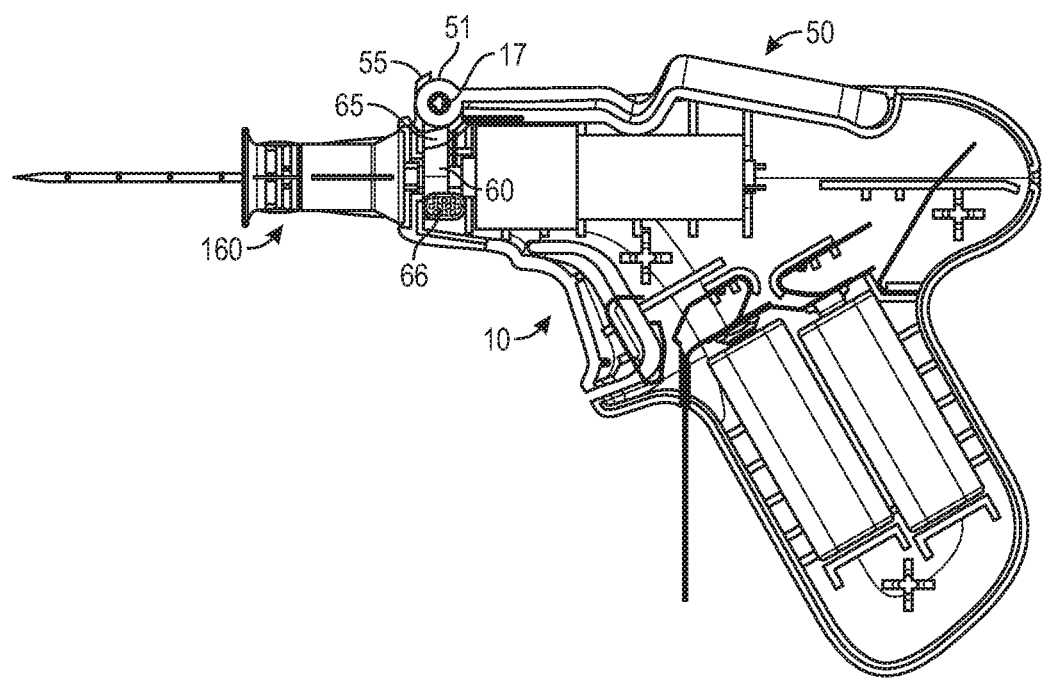
FIG. 7B illustrates a partial cross-sectional side view of the driver assembly of the present disclosure with a needle guard in a non-protective position with respect to the IO needle set of FIGS. 4A-4B coupled to a driveshaft of the driver.

A distal tip 58 of the guard member 50 may have a smooth, bulbous non-cutting surface in order to prevent injury due to accidental contact with a user. A proximal end of the guard member 50 may include a first pivot part 51 pivotably attached to a second pivot part 17 provided on the distal end 14 of the housing 12, so that the guard member can be quickly switched between a protective position as shown in FIGS. 5A-5B and a non-protective position as shown in FIGS. 7A-7B. The needle section 52 of the guard member 50 further comprises a needle groove 53 for receiving the needle portion of the IO device when the guard member is in the protective position (e.g., the needle section 52 is disposed over the cannula 210 and the stylet 220 such that the needle groove 53 receives the cannula and the stylet).

Figure 8:
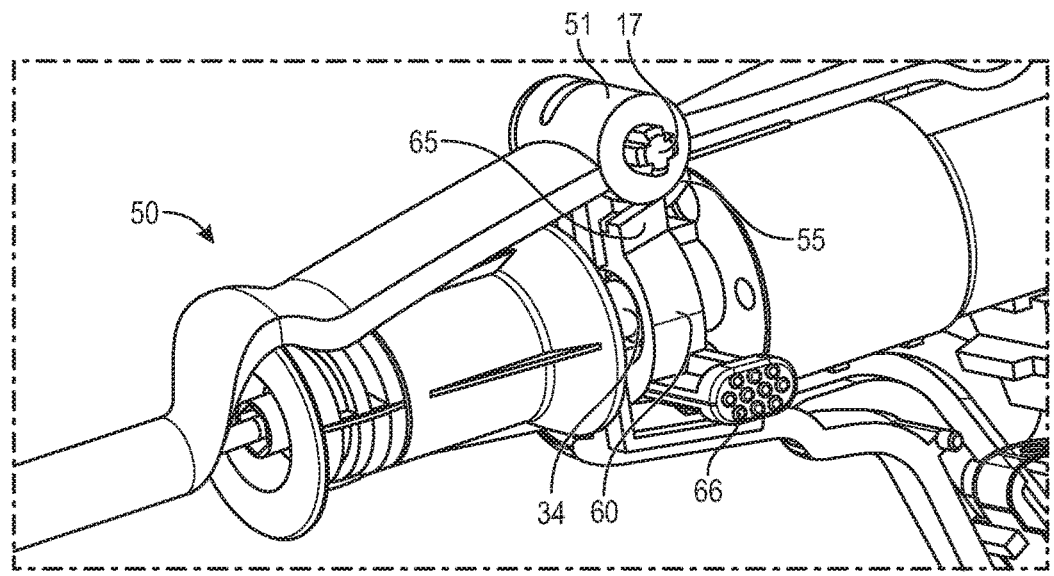
FIG. 8 illustrates a close-up isometric view of a part of the driver assembly and the IO needle set of the present disclosure with the needle guard in the protective position.

A retention collar 60 is provided inside the distal end 14 of the housing 12 and surrounds a portion of the driveshaft 34 to define an annular gap between the retention collar and the driveshaft. The retention collar 60 includes a pair of retention tabs 65 extending therefrom. The pair of retention tabs 65 are configured to engage a corresponding pair of locking notches 55 extending from the first pivot part 51 of the guard member 50 when the retention collar 60 and the driveshaft 34 are axially aligned in order to lock the guard member in the protective position, as shown in FIGS. 5A-5B and 8.

Figure 9A:
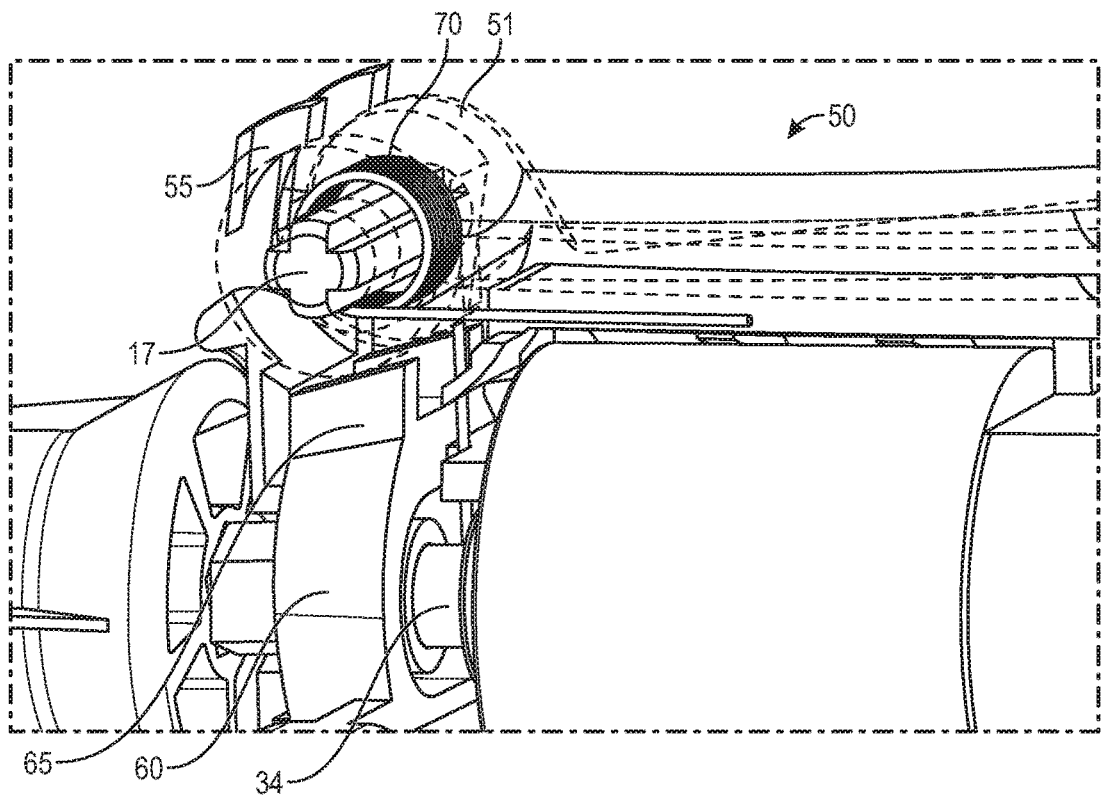
FIGS. 9A and 9B illustrate different close-up views of a part of the driver assembly of the present disclosure with a transparent view of the needle guard in the non-protective position.
Figure 9B:
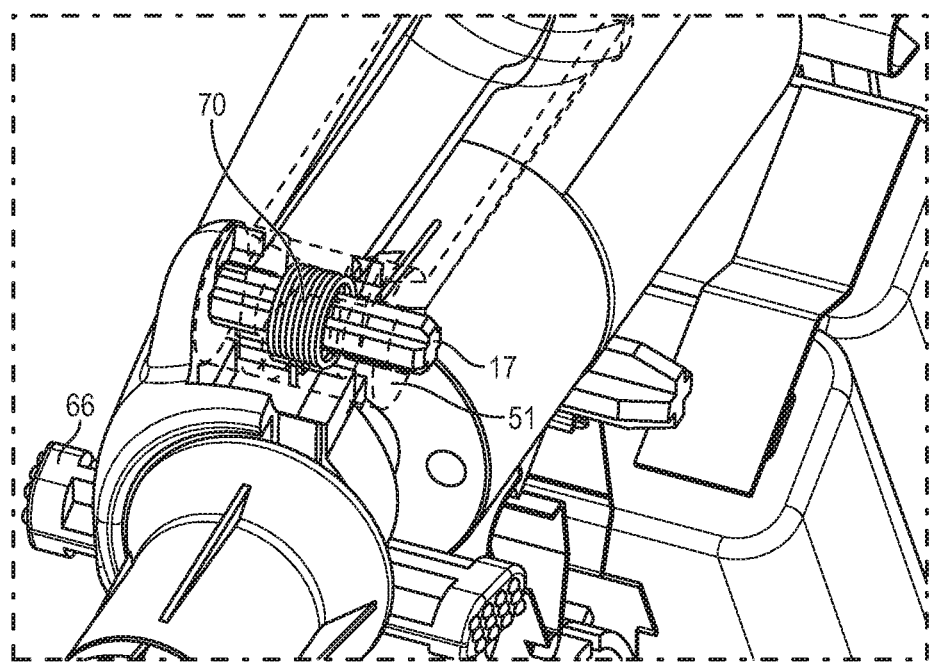

Referring to FIGS. 9A-9B, the guard member 50 is biased toward the non-protective position by a biasing element 70, such as a torsion spring, provided at the distal end 14 of the housing 12. The retention collar 60 is configured to move laterally relative to the driveshaft 34 when a release button 66 extending from the retention collar is pressed. In some implementations, the retention collar 60 may comprise a pair of release buttons 66, wherein each button of the pair of release buttons extends from opposing ends of the retention collar for ambidextrous use (e.g., so that each of the release buttons are accessible from opposing lateral sides of the housing 12 of the driver 10). Further, in some implementations, the retention collar 60, the retention tabs 65 and the pair of release buttons 66 may be integrally formed as a single piece.

During operation, a user can quickly switch the guard member 50 from its protective position shown in FIGS. 5A-5B to its non-protective position shown in FIGS. 7A-7B, by pressing either of the release buttons 66 to laterally move the retention collar 60 relative to the driveshaft 34. This movement disengages the retention tabs 65 of the collar from the locking notches 55 of the guard member 50, and thus correspondingly causes the biasing element 70 to urge the guard member to rotate about the first 51 and second 17 pivot parts. Thus, when the ambidextrous release button 66 is activated, the retention tabs 65 connected to the collar 60 slide out of contact with the corresponding locking notches 55 of the guard member 50. This activation causes the torsion spring 70 to twist, which allows the guard member 50 to flip back to align with the primary portion 13 of the housing 12. When the guard member is oriented in this non-protective position, the pre-loaded IO needle set 160 is exposed in preparation for an IO insertion.

Figure 6A:
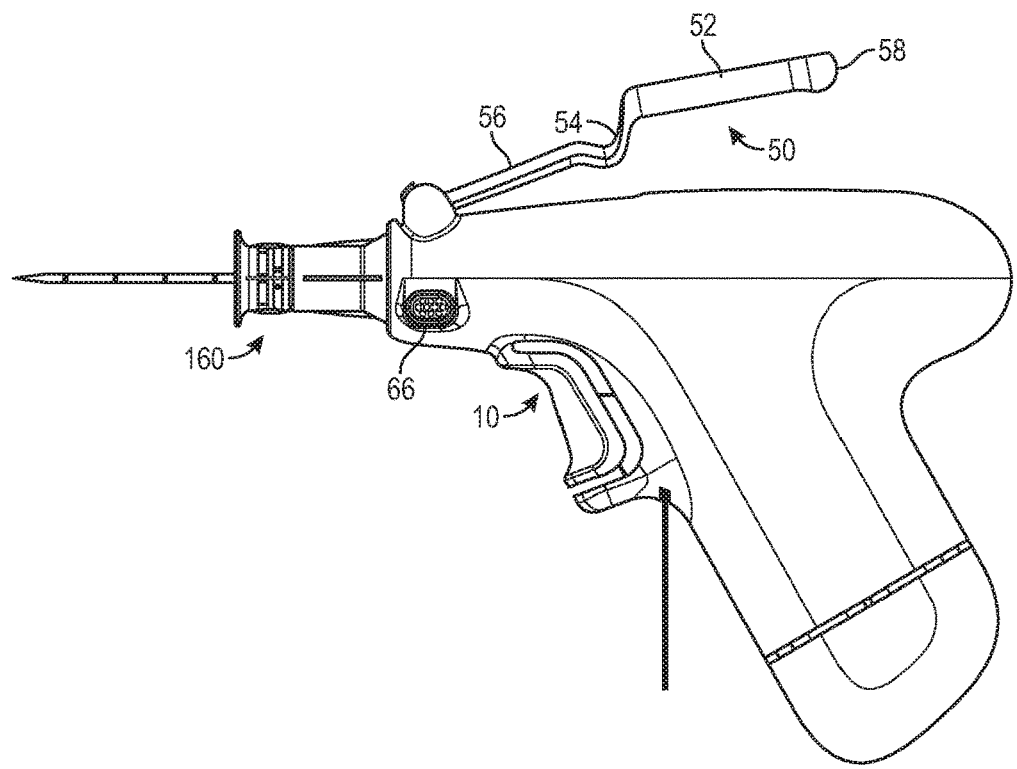
FIG. 6A illustrates a side elevation view of the driver assembly of the present disclosure with a needle guard in an intermediate position and with the IO needle set of FIGS. 4A-4B coupled to a driveshaft of the driver.
Figure 6B:
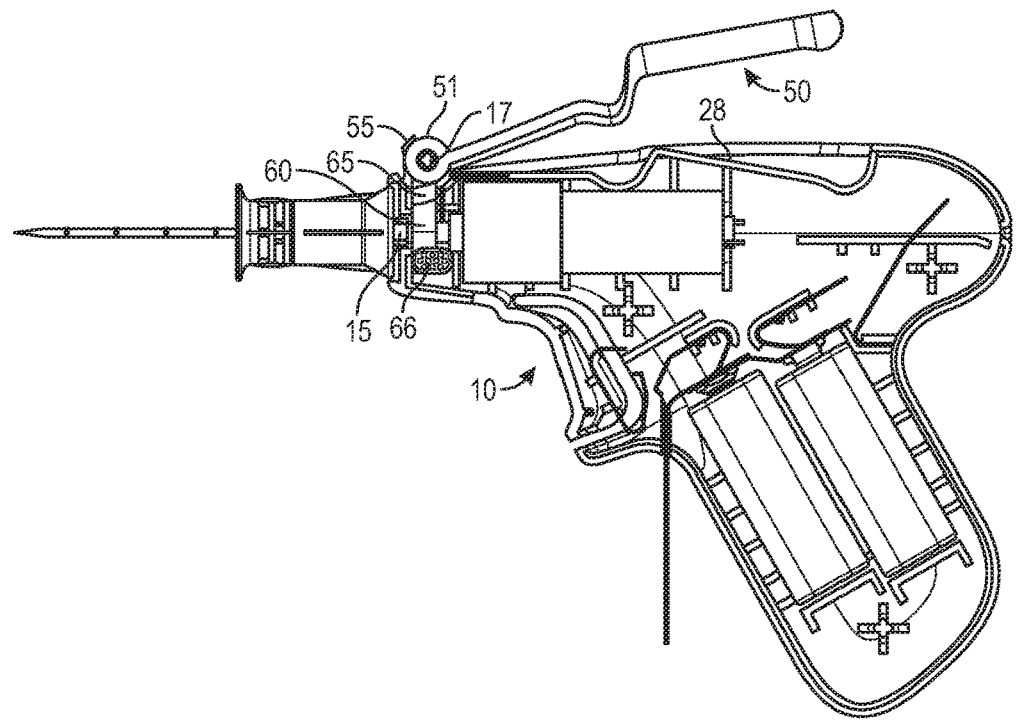
FIG. 6B illustrates a partial cross-sectional side view of the driver assembly of the present disclosure with a needle guard in an intermediate position and with the IO needle set of FIGS. 4A-4B coupled to a driveshaft of the driver.

Turning to FIGS. 6A-6B, the guard member is depicted in an intermediate position (e.g., after a user presses the ambidextrous release button 66 to disengage the retention tabs 65 from the locking notches 55 so that the biasing element 70 can begin to rotate the guard member away from its protective position and toward its non-protective position). Once the biasing element 70 has fully urged the guard member 50 to rotate to its non-protective position shown in FIGS. 7A-7B, the guard member can be received in a corresponding guard recess 28 provided along a top surface of the housing 12. The guard recess 28 is shaped to fittingly receive each of the needle section 52, the hub section 54, the connector section 56, and the distal tip 58 of the guard member 50.

Figure 10A:
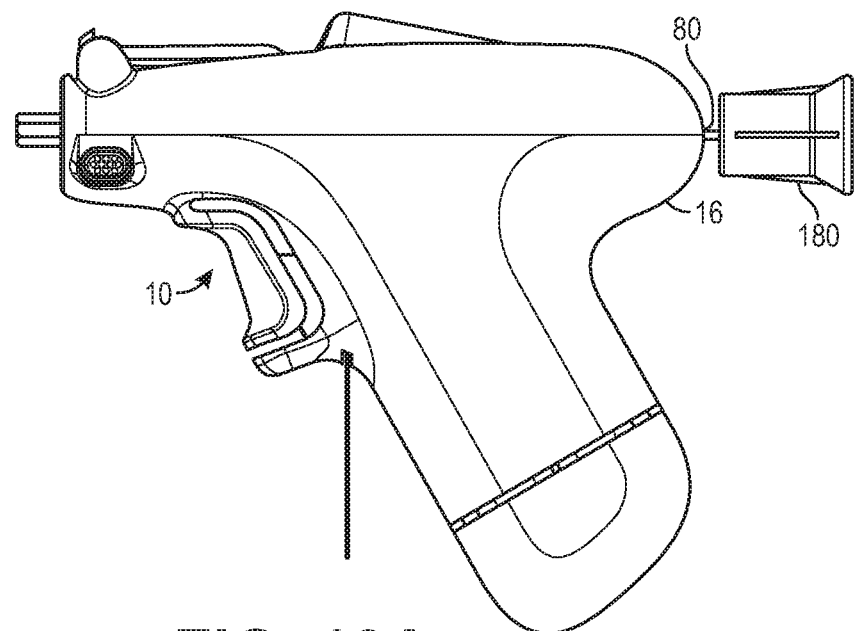
FIG. 10A depicts a side elevation view of the present driver with a needle guard in the non-protective position and with a connector of the IO needle set of FIGS. 4A-4B coupled to a sharps receptor of the driver.
Figure 10B:
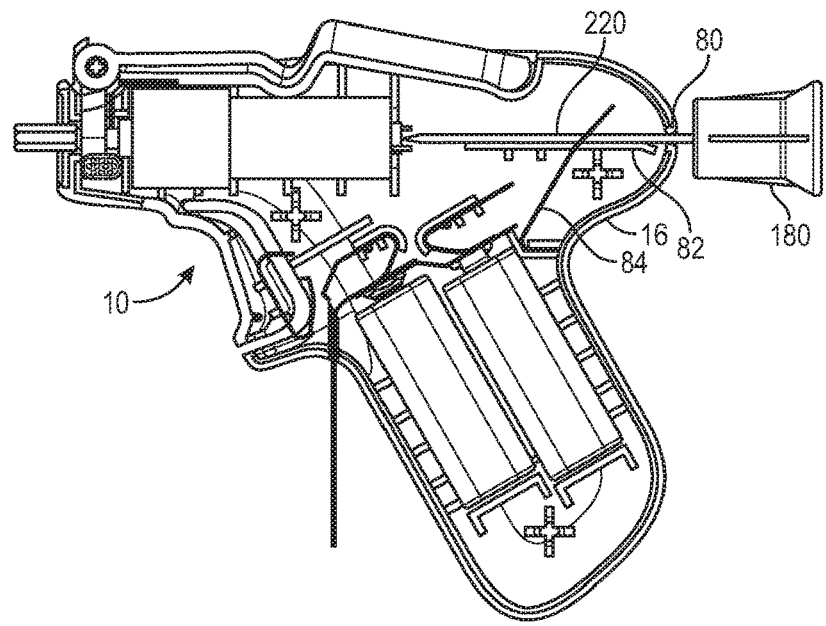
FIG. 10B depicts a partial cross-sectional side view of the present driver with a needle guard in the non-protective position and with a connector of the IO needle set of FIGS. 4A-4B coupled to a sharps receptor of the driver.
Figure 11:
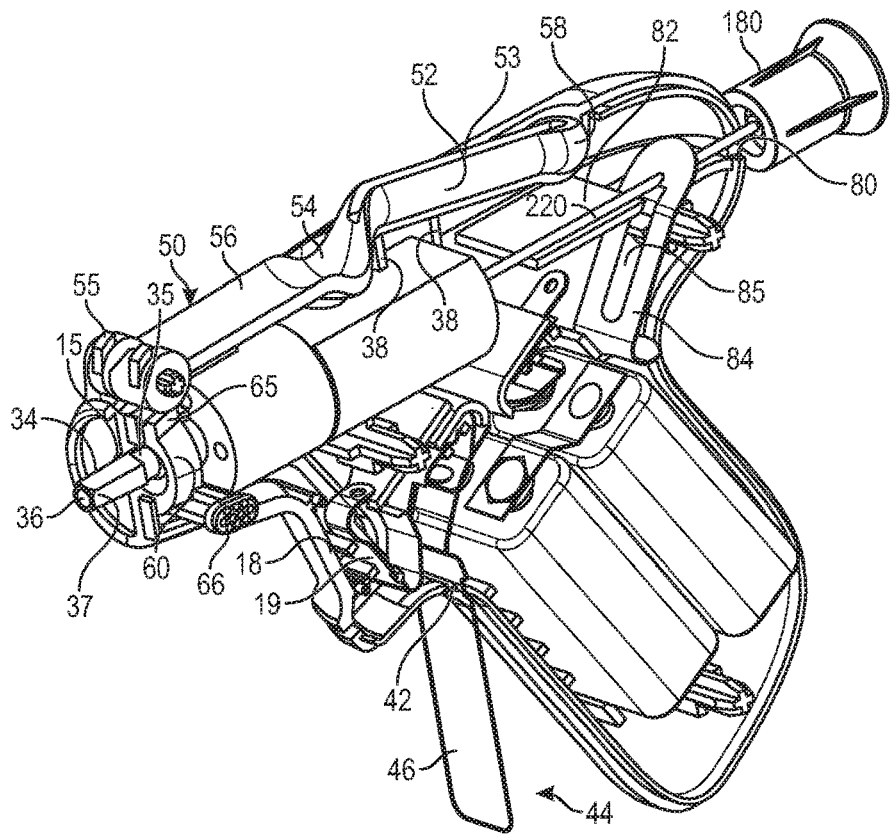
FIG. 11 depicts a perspective view of the driver of FIG. 10B with a needle guard in the non-protective position and with a connector of the IO needle set of FIGS. 4A-4B coupled to a sharps receptor of the driver.

Once the guard member 50 is rotated to its non-protective position, the driver 10 and the IO needle set 160 can then be used at a desired insertion site on a patient. Operation of the driver 10 rotates the driveshaft 34 and the IO needle set 160 to puncture skin, soft tissue, and a layer of cortical bone at the insertion site. After the driver has been used to insert a portion of the IO needle set into a target site of the patient, the user can detach the connector 180 from the hub 200. Additional components, such an IV tubing and/or a syringe, can then be attached to the hub while it remains anchored to the insertion site. While the outer penetrator 210 of the hub 200 can remain inserted in the target site of the patient, the stylet 220 of the connector 180 can be inserted through the sharps receptor 80 and into the housing of the driver as illustrated in FIGS. 10-11.

The sharps receptor 80 defines an opening at the proximal end 16 of the housing 12. An interior support shelf 82 may be fixedly located within the proximal end 16 of the housing 12 and is configured to provide support to the portion of the IO device, such as the stylet 220, that is received within the housing. A flexible sharps guide 84 may also be located within the proximal end 16 of the housing 12 and is configured to guide the portion of the IO device, such as the stylet 220, as it is received into the housing. The flexible sharps guide 84 may be configured to bias the stylet 220 against the support shelf 82. In some implementations, the sharps guide 84 may be a leaf spring.

The sharps guide 84 includes a guide slot 85 for receiving and guiding the stylet 220 as it is inserted into the housing. The interior support shelf 82 and the sharps guide 84 are both configured to securely retain the stylet within housing. In particular, the flexible sharps guide 84 may be biased toward a portion of the interior support shelf 82 so that the sharps guide correspondingly biases the stylet 220 against the support shelf as the stylet passes through the guide slot 85, thus retaining the stylet within the housing. The guide slot 85 is also configured to restrict lateral movement of the stylet 220. Accordingly, after an IO insertion of the IO needle set 160 has been completed, the user can remove the stylet 220 from the outer penetrator 210 and insert the sharp tip of the stylet 220 into the back of the housing 12 for safe disposal of the stylet with the single-use driver 10.

Figure 12:
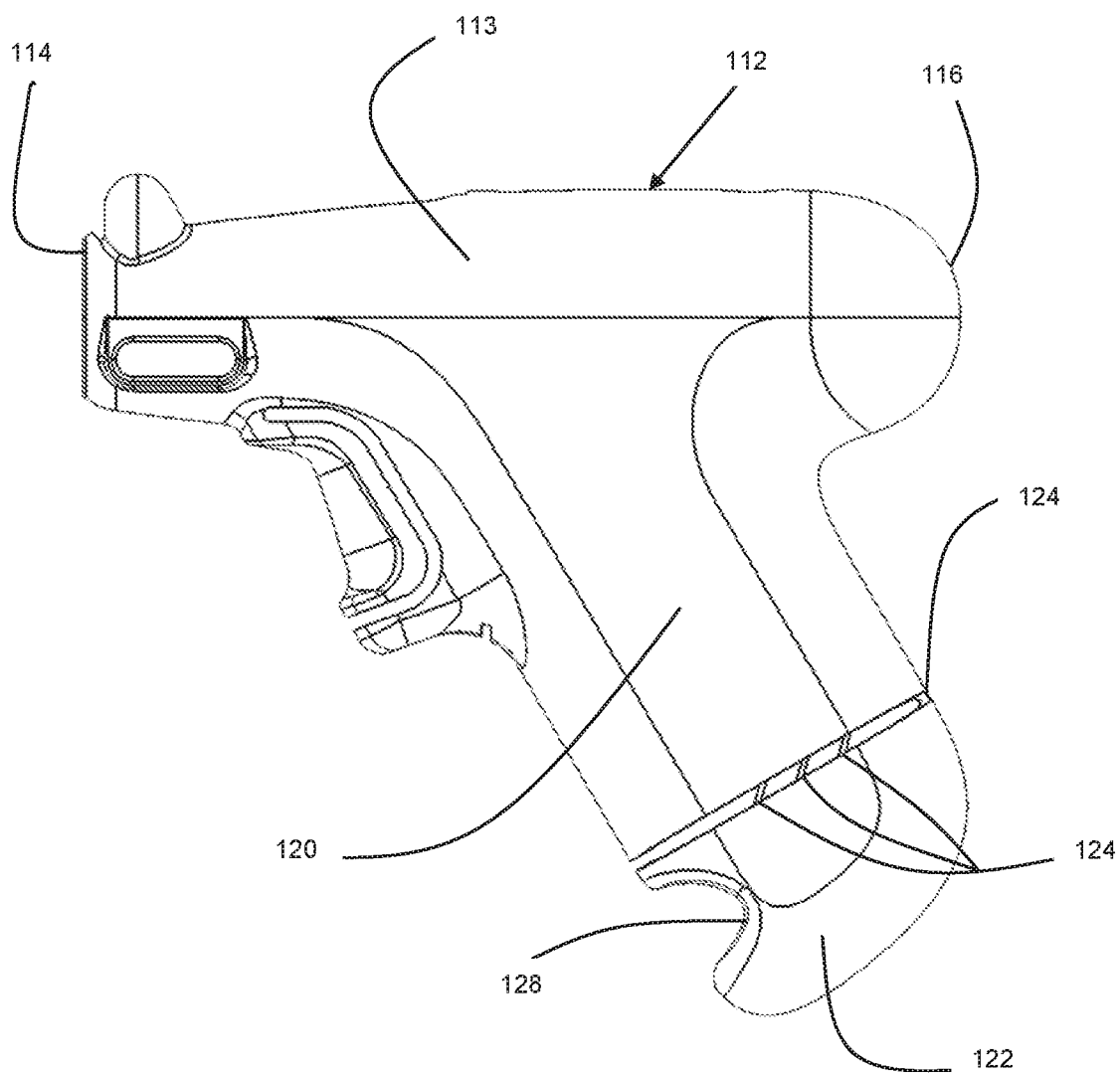
FIG. 12 depicts a side elevation view of another implementation of a driver housing having a handle with a breakable end cap.
Figure 13:
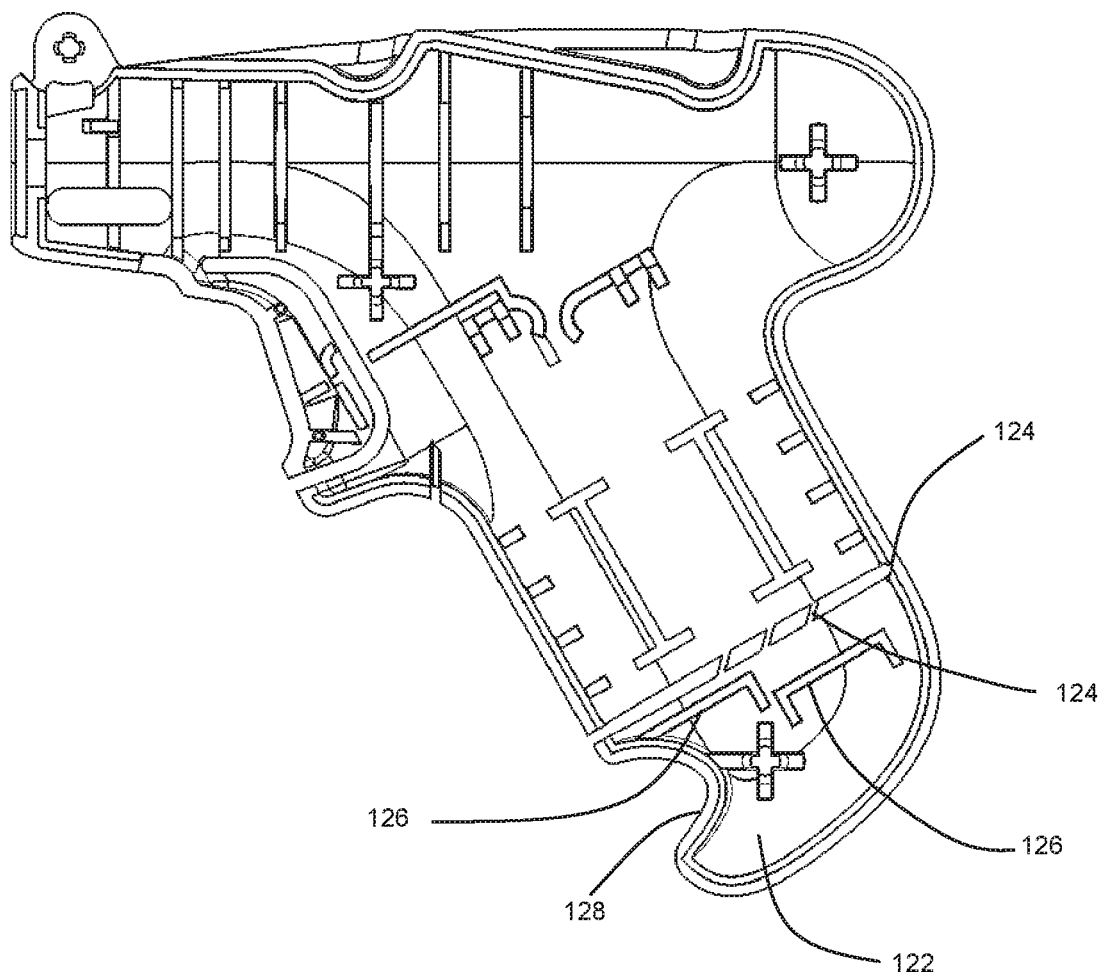
FIG. 13 illustrates a cross-sectional view of the housing shown in FIG. 12.

FIGS. 12 and 13 illustrate another implementation of a driver housing 112 which is substantially similar to the driver housing 12 previously described, with the exception of certain features described as follows. The housing 112 defines a primary portion or barrel portion 113 extending between a distal end 114 and the proximal end 116, and a handle 120 extending laterally from the primary portion 113. The handle 120 may extend from the primary portion 113 at a non-parallel angle (e.g., between thirty degrees (30°) and sixty degrees (60°), and in some embodiments, up to, including, or greater than ninety degrees (90°) relative to the longitudinal axis of the primary portion 113. In some implementations, the housing 112 and the handle 120 may have an ergonomic form factor (i.e., resembling a pistol-grip in the illustrated embodiments). The handle 120 defines an elongated, hollow compartment sized to receive a removable power source, such as batteries. The housing 112 may be formed from heavy-duty polymeric material, or other strong material. For some applications, the housing 112 may be formed in two halves which are joined together to form a fluid tight seal with various components of the driver disposed therein. For example, two halves of the housing 112 may be glued, welded, snapped, secured with screw fasteners, or otherwise coupled together such that the housing generally cannot be reopened (e.g., to replace batteries) without damaging the housing.

The driver may be configured as a single-use driver to prevent a second activation for inserting a second IO device into a patient. Preventing re-use of the driver maintains efficacy and promotes patient safety. As shown in FIG. 12, an end cap 122 is coupled to the handle 120 by at least one frangible member 124, such as a breakaway tab. Each breakaway tab 124 may be disposed on an outer periphery of the end cap 122. Each breakaway tab 124 is configured to break or snap in response to a user pulling the end cap 122 relative to the handle 120 with a sufficient amount of force. The end cap 122 further includes a grip portion 128 defining a recess sized and shaped to receive a user's thumb or other finger so that the user can laterally grip the end cap 122 in order to allow the user to rotate the end cap relative to the handle 120 to break the at least one frangible member 124, and therefore remove the end cap from the handle so that the batteries within the handle can be disposed of.

Thus, after a user completes successful insertion of an IO device into a target area of a patient, the user can manually break or snap the frangible members 124 by applying a sufficient amount of force to the end cap 122 via gripping the grip portion and pulling or rotating the end cap relative to the handle 120 in order to breakaway the end cap from the handle. The end cap 122 is not removable from the handle 120 without breaking the at least one frangible members 124. As shown in FIG. 13, the end cap 122 includes at least one internal protrusion or shelf 126 configured to support batteries within the hollow compartment of the handle 120.

Once the frangible members 124 are broken and the end cap 122 is decoupled from the handle 120, the batteries are no longer supported by the internal protrusion 126 of the end cap 122, thus causing the batteries to fall out from the hollow compartment of the handle. Moreover, once the frangible members 124 are snapped or broken, the end cap 122 can no longer be reconnected to the handle 120 without the use of some supplemental bonding or fixing element, such as adhesive. Accordingly, the driver may be used as a single-use device, whereby after insertion of the IO device in a target site of a patient is completed, the user can manually break off the end cap 122 from the handle 120 to allow easy removal and safe disposal of the batteries.

The above specification and examples provide a complete description of the structure and use of illustrative embodiments. Although certain embodiments have been described above with a certain degree of particularity, or with reference to one or more individual embodiments, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

What is claimed is:

1. A driver for inserting an intraosseous needle assembly into a bone and associated bone marrow, the driver comprising:
   a housing having a distal end and a proximal end;
   a motor disposed in the housing;
   a driveshaft extending outward from the distal end of the housing in a direction away from the proximal end;
   a gearbox coupled to the motor and to the driveshaft such that activation of the motor causes the driveshaft to rotate;
   a power source configured to power the motor;
   a guard member pivotably connected to the housing and movable between a protective position and a non-protective position, wherein the guard member is configured to cover the intraosseous needle assembly in the protective position and to expose the intraosseous needle assembly in the non-protective position; and
   a biasing member configured to urge the guard member toward the non-protective position.

2. The driver of claim 1, wherein the guard member is pivotably connected to the distal end of the housing.

3. The driver of claim 2, wherein the biasing member is a torsion spring.

4. The driver of claim 1, wherein a proximal end of the guard member includes a first pivot part, and a distal end of the housing includes a second pivot part, wherein the first and second pivot parts are configured to engage each other to allow the guard member to pivot relative to the housing.

5. The driver of claim 4, further comprising a generally cylindrical retention collar provided within the distal end of the housing and surrounding the driveshaft to define an annular gap therebetween, and wherein an axis of the retention collar is substantially aligned with an axis of the driveshaft when the guard member is oriented in the protective position.

6. The driver of claim 5, further comprising a pair of locking notches extending from the first pivot part of the guard member, and a pair of corresponding retention tabs extending upwardly from the collar, wherein the pair of locking notches are configured to engage the pair of retention tabs when the guard member is oriented in the protective position.

7. The driver of claim 6, further comprising a pair of oppositely spaced apart release buttons extending from opposed ends of the retention collar, wherein activating the pair of release buttons moves the retention collar laterally relative to the driveshaft to disengage the pair of retention tabs from contacting the corresponding pair of locking notches, thereby allowing the biasing member to pivot the guard member from the protective position to the non-protective position.

8. The driver of claim 2, wherein the guard member comprises a needle groove configured to receive an intraosseous needle.

9. The driver of claim 8, wherein the guard member comprises a distal tip having a smooth bulbous shape.

10. The driver of claim 1, further comprising a sharps receptor defining an opening provided in the proximal end of the housing and configured to receive an intraosseous needle.

11. The driver of claim 10, further comprising a flexible sharps guide and an interior support shelf, the sharps guide being located within the proximal end of the housing and configured to guide the intraosseous needle as it is received into the housing, and the interior support shelf being located within the proximal end of the housing and configured to support the intraosseous needle as it is received into the housing.

12. The driver of claim 11, wherein the sharps guide comprises a guide slot for receiving and guiding the intraosseous needle as it is inserted into the housing, and wherein the interior support shelf and the sharps guide are both configured to securely retain the intraosseous needle within the housing such that the sharps guide is biased toward the interior support shelf.

13. The driver of claim 12, wherein the sharps guide is a leaf spring.

14. The driver of claim 1, wherein the housing defines a primary portion extending between the distal end and the proximal end, and a handle extending laterally from the primary portion at a non-parallel angle relative to a longitudinal axis of the primary portion.

15. The driver of claim 14, wherein the handle defines a hollow compartment for storing the power source.

16. The driver of claim 15, further comprising an end cap connected to the handle by at least one frangible member configured to break or snap upon application of a threshold force to cause the end cap to detach from the handle, and thereby cause the power source to fall out from the compartment of the handle.

17. The driver of claim 16, wherein the end cap further includes a grip portion defining a recess sized and shaped for receiving a user's thumb or other finger so that the user can laterally grip the end cap in order to facilitate pulling or rotating the end cap relative to the handle to break the at least one frangible member.

18. The driver of claim 16, wherein the power source comprises at least one battery.

19. The driver of claim 2, wherein a top surface of the housing comprises a guard recess having a shape corresponding to the shape of the guard member for receiving the guard member when in the non-protective position.

20. A method for inserting an intraosseous needle assembly into a bone and associated bone marrow, the method comprising:
providing a driver according to claim 1, the intraosseous needle assembly being coupled to a driveshaft of the driver, and the driver having a guard member oriented in a protective position;
manipulating a retention collar to pivot the guard member from the protective position to a non-protective position;
disposing a distal end of the intraosseous needle assembly at a desired insertion site on a patient;
actuating a trigger of the driver to activate the motor to rotate the driveshaft and the intraosseous needle assembly;
inserting a portion of the intraosseous needle assembly into the insertion site;
applying an amount of force to an end cap of a handle of the driver to detach the end cap and remove the power source; and
removing a component of the needle assembly from the insertion site and inserting the component into a sharps receptor provided in the housing of the driver.

* * * * *